United States Patent [19]

Lafon

[11] Patent Number: 4,545,996

[45] Date of Patent: Oct. 8, 1985

[54] N-(4-ACETYLAMINOPHENACYL)AMINE DERIVATIVES USEFUL AS PHARMACEUTICALS

[75] Inventor: Louis Lafon, Paris, France

[73] Assignee: Laboratoire L. Lafon, France

[21] Appl. No.: 660,284

[22] Filed: Oct. 12, 1984

[30] Foreign Application Priority Data

Oct. 14, 1983 [FR] France ................................ 83 16405

[51] Int. Cl.⁴ .......................................... C07C 103/127
[52] U.S. Cl. ..................................... 514/629; 564/218
[58] Field of Search ......................... 564/218; 424/324

[56] References Cited

U.S. PATENT DOCUMENTS 3,352,904 11/1967 Bicking et al. ................... 564/218 X
3,555,091 1/1971 Benoit-Guyod et al. ............ 564/218
4,032,573 6/1977 Kaneko et al. ................. 564/218 X

FOREIGN PATENT DOCUMENTS 0081207 12/1982 European Pat. Off. ............ 564/218

*Primary Examiner*—Paul F. Shaver
*Attorney, Agent, or Firm*—Cantor and Lessler

[57] ABSTRACT

The present invention relates, by way of new industrial products, to the N-(4-acetylaminophenacyl)-alkylamines of the general formula

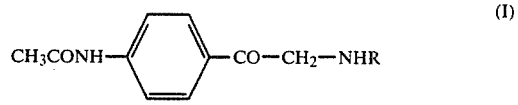

in which R is isopropyl or tert.-butyl, and their addition salts.

These new products are useful in therapy, especially as antidepressants for the CNS.

6 Claims, No Drawings

N-(4-ACETYLAMINOPHENACYL)AMINE DERIVATIVES USEFUL AS PHARMACEUTICALS

The present invention relates to new N-(4-acetylaminophenacyl)amine derivatives as industrial products. It also relates to their use in therapy, especially as antidepressants and psychostimulants, and to the method for their preparation.

It is known that phenacylamine derivatives have already been described and their therapeutic properties studied. N-(2,4,6-Trihydroxyphenacyl)isopropylamine and N-(2,4,6-trimethoxyphenacyl)piperazine, which have been proposed as peripheral vasodilators, are known in particular from U.S. Pat. No. 3,895,030, and N-(2,4,6-trimethoxyphenacyl)isopropylamine and N-(2,4,6-trimethoxyphenacyl)tert.-butylamine, which have been recommended as sedatives, aggression inhibitors and antidepressants for the central nervous system (CNS), are known from French Patent Application No. 2,503,143.

Surprisingly, it has just been found that, compared with the abovementioned phenacylamine derivatives, the compounds according to the invention, which are structurally different, are more valuable in therapy, especially as antidepressants for the CNS. In particular, N-(4-acetylaminophenacyl)isopropylamine hydrochloride (CRL 41 021) according to the invention is less toxic (LD-50=1800 mg/kg administered orally to male rats) and more active as an antidepressant (DTD-daily treatment dose for man in order to have the antidepressant effect-3 mg) than the N-(2,4,6-trimethoxyphenacyl)isopropylamine hydrochloride known in the prior art (LD-50=450 mg/kg administered orally to male rats; DTD=30 mg).

The new phenacylamine derivatives according to the invention are selected from the group consisting of (i) the N-(4-acetylaminophenacyl)alkylamines of the general formula

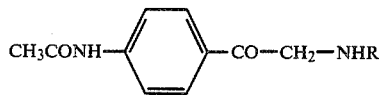

(I)

in which R is a group CH(CH$_3$)$_2$ or C(CH$_3$)$_3$; and (ii) their addition salts.

The expression "addition salts" is understood here as meaning firstly the acid addition salts obtained by reacting the free base of the formula I with inorganic or organic acids, and secondly the ammonium salts. Hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular among the acids which can be used to salify the base of the formula I. CH$_3$I and CH$_3$Cl may be mentioned in particular among the compounds making it possible to obtain ammonium salts. In general terms, the acid addition salts are preferred to the ammonium salts.

A number of compounds according to the invention have been collated in Table I below without in any way implying a limitation.

TABLE I

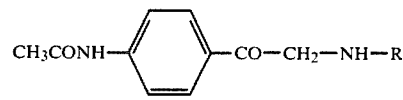

| Product | Code No. | R |
|---|---|---|
| Example 1 (a) | CRL 41 021 | CH(CH$_3$)$_2$ |
| Example 2 (a) | — | C(CH$_3$)$_3$ |
| Example 3 (b) | — | CH(CH$_3$)$_2$ |
| Example 4 (c) | — | CH(CH$_3$)$_2$ |

Notes
(a): hydrochloride
(b): fumarate
(c): methanesulfonate

The compounds according to the invention can be prepared in accordance with a method known per se, by the application of classical reaction mechanisms. The method recommended here consists in reacting a 4-acetylaminophenacyl halide of the formula

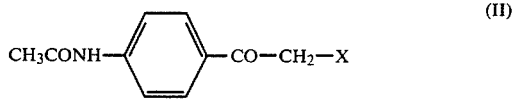

(II)

in which X is Cl or Br, with a primary amine of the formula

H$_2$NR (III)

in which R is defined as indicated above.

This reaction is carried out by reacting one mol of halide II with more than one mol of amine III. Advantageously, 1 mol of II will be reacted with 1.5 to 5 mol of III in an inert solvent, for at least 1 hour, at a temperature of between 15° and 40° C.

The compounds of the formula I and their salts are useful in neuropsychopharmacology on account of their antidepressant and psychostimulant properties. According to the invention, a therapeutic composition is recommended which contains, in association with a physiologically acceptable excipient, at least one compound of the formula I or one of its non-toxic addition salts as the active principle.

Of course, in a composition of this type, the active principle is present in a pharmaceutically effective quantity.

Further advantages and characteristics of the invention will be understood more clearly on reading the following description of preparative examples and results of pharmacological tests; these data as a whole do not imply a limitation but are given by way of illustration.

PREPARATION I

Preparation of
N-(4-acetylaminophenacyl)isopropylamine hydrochloride

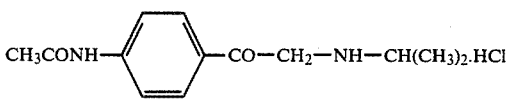

(Example 1; Code No.: CRL 41 021)

In a reactor, 21 g (0.1 mol) of 4-acetylaminophenacyl chloride are introduced into a mixture comprising 100 ml of dioxane, 26 ml (0.3 mol) of isopropylamine and 20 ml of water. The reaction medium is stirred at 30°–40° C. for 2 hours. After the addition of 500 ml of iced water, a precipitate is collected, washed and dried. Recrystallization from ethyl acetate gives 21 g of N-(4-acetylaminophenacyl)isopropylamine, which is in the form of a white powder. Melting point (inst.) = 156° C.

The 21 g of free base thus obtained are dissolved in 200 ml of acetone. Precipitation by means of a stream of HCl gas gives 20 g of CRL 41 021 (yield: 73.9% relative to the 4-acetylaminophenacyl chloride) in the form of a white powder. Melting point (inst.) > 250° C.

PREPARATION II

Preparation of N-(4-acetylaminophenacyl)tert.-butylamine hydrochloride (Example 2)

By following the procedure indicated in Preparation I and replacing the isopropylamine with tert.-butylamine, N-(4-acetylaminophenacyl)tert.-butylamine hydrochloride is obtained.

PREPARATION III

Preparation of N-(4-acetylaminophenacyl)isopropylamine methanesulfonate (Example 4)

The N-(4-acetylaminophenacyl)isopropylamine obtained according to Preparation I is reacted with methanesulfonic acid to give N-(4-acetylaminophenacyl)isopropylamine methanesulfonate.

The results of the tests which were undertaken with the product of Example 1, which is the preferred compound according to the invention, have been summarized below.

A. TOXICITY

The LD-50 on oral administration to Sprague Dawley rats is 1550±54 mg/kg for the females and 1800±139 mg/kg for the males.

B. NEUROPSYCHOPHARMACOLOGICAL STUDY

I. INVESTIGATION OF STEREOTYPE MOVEMENTS

Groups of 6 rats receive an intraperitoneal injection of CRL 41 021 or of distilled water immediately before being placed in small cages, where their stereotype behavior is noted every 10 minutes until the effect wears off. It is observed that, as from a dose of 32 mg/kg, CRL 41 021 causes the appearance of stereotype movements in rats. The intensity of this effect increases with the dose and, at 64 mg/kg, reaches a level comparable to that obtained with 2 mg/kg of amphetamine.

II. INTERACTION WITH APOMORPHINE

1°. In mice

Groups of 6 mice receive CRL 41 021 by intraperitoneal administration half an hour before the subcutaneous injection of 1 or 16 mg/kg of apomorphine. It is found that, at doses of 64 and 256 mg/kg, CRL 41 021 exerts an intrinsic hypothermic effect and does not modify the hypothermia, righting behavior and stereotypies induced by apomorphine in mice.

2°. In rats

CRL 41 021 is administered intraperitoneally to groups of 6 rats half an hour before the subcutaneous injection of 0.5 mg/kg of apomorphine. It is found that, at doses of 32 and 128 mg/kg, CRL 41 021 causes a distinct potentiation of the stereotypies induced by apomorphine in rats.

III. INTERACTION WITH AMPHETAMINE

Amphetamine (2 mg/kg) is injected intraperitoneally into groups of 6 rats half an hour after the intraperitoneal administration of CRL 41 021. It is found that, at the strongest dose used (128 mg/kg), CRL 41 021 distinctly potentiates the stereotypies induced by amphetamine.

IV. INTERACTION WITH RESERPINE

Four hours after the intraperitoneal injection of 2.5 mg/kg of reserpine, groups of 12 mice receive CRL 41 021 by intraperitoneal administration for the purpose of studying the action of the product on temperature and ptosis. It is observed that, at doses of 64 mg/kg and 256 mg/kg, CRL 41 021 distinctly counteracts the hypothermia induced by reserpine, whereas the ptosis induced by reserpine is only slightly antagonized at the strongest dose (256 mg/kg). The antagonism of the hypothermia only develops after a latency of about one hour.

V. INTERACTION WITH OXOTREMORINE

CRL 41 021 is administered intraperitoneally to groups of 6 mice half an hour before the intraperitoneal injection of 0.5 mg/kg of oxotremorine.

1°. Action on the temperature

At a strong dose (128 mg/kg), CRL 41 021 exerts a hypothermic effect and only counteracts weakly (and nonsignificantly) the temperature drop induced by oxotremorine.

2° Action on the trembling

The trembling due to oxotremorine is not modified by CRL 41 021.

3°. Action of the peripheral cholinergic symptoms

CRL 41 021 does not modify salivation and lacrimation, but seems (at doses of 16, 64 and 256 mg/kg) to reduce the incidence of defecation.

VI. ACTION ON THE FOUR PLATE TEST, TRACTION AND ELECTRIC SHOCK

The test is performed on groups of 10 mice half an hour after the intraperitoneal administration of CRL 41 021. It is observed that CRL 41 021 does not cause an increase in the number of punished passes, that it does not cause major deficiency and that, at a strong dose (256 mg/kg), it partially opposes the convulsant effects of electric shock.

VII. ACTION OF THE SPONTANEOUS MOTILITY

Half an hour after they have received CRL 41 021 by intraperitoneal administration, the mice (12 per dose, 24 control animals) are placed in an actimeter, where their motility is recorded for 30 minutes. It is found that, at doses of 16 and 64 mg/kg, CRL 41 021 causes hypermotility. This effect disappears at a stronger dose (256 mg/kg).

VIII. ACTION OF THE INTERGROUP AGGRESSION

After they have stayed for 3 weeks in the two halves of a cage divided by an opaque partition, groups of 3 mice receive CRL 41 021 by intraperitoneal administration. Half an hour later, the two groups from the same cage are brought together by removal of the partition, and the number of fights which occur in 10 minutes is noted. It is noted that, at a dose of 256 mg/kg, CRL 41 021 reduces the number of fights despite (or because of) subjectively observed excitation.

IX. ACTION TOWARDS SOME FORMS OF BEHAVIOR PERTURBED BY VARIOUS AGENTS

1° Motility reduced by habituation to the enclosure

After they have stayed in the actimeters for 18 hours, the mice (6 per dose, 12 control animals) receive CRL 41 021 by intraperitoneal administration. They are immediately returned to their respective enclosures and, half an hour later, their motility is recorded for 30 minutes. It is observed that, at doses of 16 mg/kg, 64 mg/kg and 256 mg/kg, CRL 41 021 causes a resumption in the activity of mice accustomed to their enclosure.

2° Motility reduced by hypoxic aggression

Half an hour after they have received CRL 41 021 by intraperitoneal administration, the moce (10 per dose, 20 control animals) are subjected to acute hypobaric anoxia [pressure reduction of 600 mm Hg (i.e. about $8 \times 10^4$ pascals) in 90 seconds; release of vacuum in 45 seconds] and are then placed in an actimeter, where their motility is recorded for 10 minutes. It is observed that, at the strongest dose used (256 mg/kg), CRL 41 021 causes a substantial improvement in the motor recovery in mice whose motility has been depressed following a brief period in a reduced-pressure enclosure.

3° Asphyxiant anoxia

Groups of 10 mice receive CRL 41 021 by intraperitoneal administration half an hour before the intraperitoneal administration of 32 mg/kg of gallamine triiodoethylate (reference curarizing agent). It is observed that, at a strong dose (256 mg/kg), CRL 41 021 tends to delay the occurrence of death following asphyxiant anoxia caused by a curarizing agent.

X. INTERACTION WITH BARBITAL

Half an hour after the intraperitoneal administration of CRL 41 021, groups of 10 mice receive an intraperitoneal injection of barbital (220 mg/kg). It is found that, as from a dose of 4 mg/kg, CRL 41 021 reduces the duration of the sleep induced by barbital. The maximum effect is obtained at doses of 64 to 256 mg/kg.

XI. ACTION OF THE "BEHAVIORAL DESPAIR"

Half an hour after they have received CRL 41 021 by intraperitoneal administration, groups of 6 male mice are placed in a beaker filled with water to a height of 6 cm. The total period of immobility between the 2nd and 6th minutes following immersion is noted. It is observed that, at a dose of 16 mg/kg, CRL 41 021 moderately reduces the period of immobility or so-called period of "despair". This effect is greater at doses of 64 to 256 mg/kg.

XII. INVESTIGATION OF A PARTICULAR TOXICITY IN GROUPED MICE

Immediately after the intraperitoneal administration of CRL 41 021, groups of 10 mice are placed in small cages. The number of dead animals is noted every hour for 4 hours and then after 24 hours. The toxicity of CRL 41 021 is determined under the same conditions with one mouse per cage. It is observed that CRL 41 021 is not more toxic to the isolated mice than to the grouped mice.

C. CARDIOVASCULAR STUDY

CRL 41 021 was studied on two types of animals:
a. anesthetized normotensive rats,
b. anesthetized, pithed, atropinized, bivagotomized normotensive rats.

The product was administered intravenously (jugular vein) in physiological solution prepared cold, in a volume of 1 ml/kg of weight.

I. IN ANESTHETIZED RATS

The effect of a range of doses from 0.1 to 30 mg/kg, administered intravenously at 10-minute intervals, was studied on the mean blood pressure and the heart beat.

At the doses studied, CRL 41 021 does not exert any action on the mean blood pressure or on the heart beat of anesthetized rats. On the other hand, it potentiates the hypertensive response to two doses of noradrenaline (0.5 and 1 µg/kg) administered after 30 mg/kg, compared with the control responses. The reflex bradycardia is also increased in duration and in intensity. It is also observed that the potentiation of the response to phenylephrine (1 and 2 µg/kg) is more doubtful.

II. IN PITHED ANESTHETIZED RATS

1° Action on the mean blood pressure and heart beat

The same range of doses was studied in pithed anesthetized rats as in the non-pitched rats. It is found that CRL 41 021 does not exert any action on the mean blood pressure or on the heart beat of pithed rats.

2° Action towards noradrenaline and phenylephrine

Doses of 3 mg and 30 mg/kg of CRL 41 021, administered intravenously, potentiate the hypertensive response to noradrenaline and phenylephrine in intensity and in duration. On the other hand, no modification of the effects is observed on the heart beat of the animals treated with noradrenaline and phenylephrine.

3° Action towards the hypertension due to stimulation of the spinal cord at increasing frequency Doses of 3 and 30 mg/kg of CRL 41 021 have no effect on the hypertension due to electrical stimulation of the spinal cord at high frequencies (2 Hz, 5 Hz, 10 Hz) for 30 seconds; however, taking into account the decrease in the response with time in the case of the control animals, it may be considered that the responses after 3 and 30 mg/kg of CRL 41 021 are slightly potentiated.

4° Action towards the tachycardia due to continuous stimulation of the spinal cord at low frequency CRL 41 021 is studied at doses of 0.1 to 30 mg/kg, administered intravenously, on 5 rats whose spinal cord is stimulated by a low-frequency (1 Hz) current for 30 minutes.

The tachycardia due to electrical stimulation is partially antagonized by the intravenous administration of 30 μg/kg of clonidine 5 minutes after the start of stimulation. The injections of the range of doses of CRL 41 021 are carried out every 2 minutes, starting 5 minutes after the clonidine. It is observed that CRL 41 021 partially restores the tachycardia due to stimulation and antagonized by clonidine, as from a dose of 0.3 mg/kg administered intravenously.

D. CONCLUSIONS

The results of the neuropsychopharmacological tests show that CRL 41 021 is a stimulant which differs from the amphetamine stimulants by its absence of group toxicity, its antagonism of hypothermia and the absence of signs of sympathetic stimulation.

The results of the cardiovascular tests demonstrate that CRL 41 021 has no effect on the mean blood pressure and the heart beat up to a dose of 30 mg/kg, administered intravenously, on pithed or non-pithed anesthetized rats. The restoration of the tachycardia produced by continuous stimulation of the spinal cord of rats at low frequency, and antagonized by clonidine, demonstrates that CRL 41 021 has an $\alpha^-$presynaptic action; finally, the potentiation of phenylephedrine seems to suggest an action on the $\alpha_1$ postsynaptic receptors.

In clinical trials, good results were obtained on man after the administration of CRL 41 021, as an antidepressant, in the form of tablets or gelatine capsules each containing 1 mg of CRL 41 021, at a rate of 3 tablets or gelatine capsules per day for at least one week, in the treatment of depressive states.

What is claimed is:

1. A N-(4-acetylaminophenacyl)amine derivative useful especially in therapy, which is selected from the group consisting of:

(i) the N-(4-acetylaminophenacyl)alkylamines corresponding to the general formula:

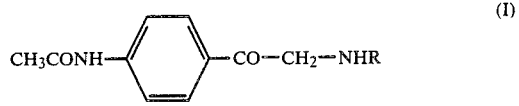

(in which R represents an isopropyl or tert.-butyl group), and (ii) their addition salts.

2. N-(4-Acetylaminophenacyl)isopropylamine and its addition salts.

3. N-(4Acetylaminophenacyl)tert.-butylamine and its addition salts.

4. A therapeutic composition which contains, in association with a physiologically acceptable excipient, at least one N-(4-acetylaminophenacyl)alkylamine derivative of the formula (I) as claimed in claim 1, or one of its non-toxic addition salts.

5. A method for the preparation of a compound of the formula (I) as claimed in claim 1, which comprises reacting 1 mol of a 4-acetylaminophenacyl halide of the formula:

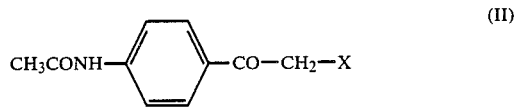

in which X is Cl or Br, with more than one mol of an amine of the formula $$H_2NR \qquad (III)$$

in which R is isopropyl or tert.-butyl.

6. The method as claimed in claim 5, wherein 1 mol of halide II is reacted with 1.5 to 5 mol of amine III, for at least 1 hour, at a temperature of between 15° and 40° C.

* * * * *